(12) United States Patent
Regas et al.

(10) Patent No.: US 6,364,844 B1
(45) Date of Patent: Apr. 2, 2002

(54) DIAGNOSTIC SYSTEM FOR DETERMINING AND/OR MONITORING PHYSIOLOGICAL CONDITIONS IN MAMMALS

(76) Inventors: Jennine Regas, 12395 E. Cedar Cir., Aurora, CO (US) 80012; Philip George Chelf Regas, 6909 Willow St., Falls Church, VA (US) 22046

(\*) Notice: Subject to any disclaimer, the term of this patent is extended or adjusted under 35 U.S.C. 154(b) by 0 days.

(21) Appl. No.: 09/691,185

(22) Filed: Oct. 19, 2000

(51) Int. Cl.⁷ .............................................. A61B 5/00
(52) U.S. Cl. ..................................................... 600/551
(58) Field of Search ............................... 600/551, 587, 600/591

(56) References Cited

U.S. PATENT DOCUMENTS

| | | | | |
|---|---|---|---|---|
| 4,685,471 A | \* | 8/1987 | Regas et al. | 600/551 |
| 4,770,186 A | \* | 9/1988 | Regas et al. | 600/551 |
| 4,836,216 A | \* | 6/1989 | Fernando et al. | 600/551 |
| 5,685,319 A | \* | 11/1997 | Maret | 600/551 |
| 5,837,197 A | \* | 11/1998 | Porrazzo et al. | 600/551 |

\* cited by examiner

*Primary Examiner*—Max Hindenburg
(74) *Attorney, Agent, or Firm*—James L. Wilcox

(57) ABSTRACT

Improvements in a diagnostic system for determining and/or monitoring a physiological condition in a female mammal are disclosed. The system comprises:

(a) a read only memory means for storing a diagnostic program for determining the fertility state of the female subject from salivary and vaginal resistance data values, (b) a random access memory means for storing temporary data values;

(c) a non-volatile memory means for storing daily data values;

(d) a display means for displaying characters representing the fertility state;

(e) a microprocessor means for controlling the processing of data in accordance with said diagnostic program, said microprocessor means being connected to read only memory means, said random access memory means, said nonvolatile memory means, and said display means;

(f) a sensing means for sensing the resistance of an electrical path along the tongue or vagina of the female user and outputting analog signals, (g) a conversion means for converting said analog signals to digital signals;

(h) an input means for enabling the input of data by the female subject; and (i) a first interface means connected to said input means and said analog-to-digital conversion means for enabling the input of digital signals representing a current daily data value to said microprocessor means. The diagnostic program comprises algorithms for the recognition of predetermined patterns of data values, said algorithms being applied to said current daily data value and said stored daily data values by said microprocessor means, said microprocessor means controlling said display means to display characters representing one of several fertility states of said subject in response to recognition of a corresponding one of said predetermined patterns. The improvements involve the algorithms being capable of determining, substantially automatically, variables that can be used to define the beginning of the fertile cycle of the mammal, the end of the fertile cycle of the mammal and the most fertile day of the mammal.

23 Claims, No Drawings

DIAGNOSTIC SYSTEM FOR DETERMINING AND/OR MONITORING PHYSIOLOGICAL CONDITIONS IN MAMMALS

BACKGROUND OF THE INVENTION

1. Technical Field

This invention relates generally to the field of determining and/or monitoring physiological conditions in mammals, and in particular relates to electronically sensing, predicting and confirming that such physiological conditions exist in female mammals. The invention also particularly relates to an improved means and method for predicting and confirming ovulation in human females that offers enhanced features and advantages over prior methods, such as substantial automation, greater reliability, more accurate results and enhanced ease of use, enabling a correspondingly greater acceptance as the method of choice for fertility prediction, and birth control, by consumers and organizations.

2. Background Art

The problem of determining the precise point when ovulation in mammals has occurred is of ever-increasing interest throughout the world, both in the animal husbandry industry and with respect to humans. It is especially important for human couples suffering from infertility to determine if and when ovulation occurs, to maximize the potential for pregnancy. At ovulation, an egg is released from the ovary. This egg remains viable approximately 12–24 hours. Conception occurs when an egg, present in the fallopian tube, is fertilized by a sperm. However, the egg is present in the fallopian tube typically for only a few hours, usually from 3–10. Meanwhile, sperm remains viable in a female for up to 48 hours. Thus, if a woman wishes to become pregnant it is necessary for the sperm and egg to interact within the 12–24 hours following ovulation.

Meanwhile, for other couples who desire to practice family planning or minimize the potential for pregnancy by monitoring the female ovulation cycle, it is possible to determine that portion of the month where conception is physically impossible. Thus, both infertility and birth control may be impacted by the ovulation cycle.

There are many types of tests known in the art that can be conducted for the purpose of predicting the time of ovulation. For example, one well-known test is designed to predict ovulation by comparing the pH in a woman's saliva with that of her vagina over the course of time. By comparing the changes in the pH levels of a woman's body, it is scientifically possible to predict when ovulation will occur. Such a test employs a device similar to a digital pH meter, which permits a determination of the pH of a solution. Similarly, tests are well known for measuring the level of luteinizing hormone in various body fluids, as a predictor of ovulation occurrence. These tests typically either include a urine test or a blood test. Luteinizing hormone is a hormone of protein-carbohydrate composition that is obtained from the interior lobe of the pituitary gland, and that in the female, stimulates the development of corpora lutea, and together with follicle stimulating hormone, the secretion of progesterone. The luteinizing hormonal level in the blood peaks just before ovulation and drops after ovulation.

Other methodologies of the prior art rely on the concept that it is possible to predict when ovulation has occurred, based on the well-known basal body temperature increase in a female (up to 1 degree Fahrenheit) shortly after the time of ovulation. Still another methodology involves "ferning" of the cervical mucus. The optimal time for conception is thought to be when the cervical mucus is at its maximum density. Medical personnel, in conjunction with a pelvic exam, can examine mucus which has been deposited on a slide under a microscope to determine the amount of "ferning." Whereas the normal amount of "ferning" ranges from 1–3, optimal conditions for conception exist when the value associated with "ferning" is 4+.

Attempting to conduct all of the tests described above is both time consuming, relatively expensive, and requires the assistance of medical professionals. However, to verify that optimum conditions exist, in the usual case all of the above tests should be performed and should test positive.

The need for a simple but reliable method of predicting and confirming ovulation, which can be conveniently carried out in the privacy of the home, has been a recognized need for many decades. Because of religious, philosophic, or health considerations, the preferred method of birth control for many is by periodic abstinence, also known as the "rhythm method." This method involves the identification of the fertile period using an available method, or more often simply by a guess based on the length of the menstrual cycle, and then avoiding coitus during this period. Ovulation is assumed to occur mid-cycle, and the period of abstinence is adjusted accordingly. This technique has proven highly unreliable at best. The unreliability of the rhythm method is largely due to the inability to accurately predict and confirm ovulation. Thus, a clear need exists for a natural family planning method, acceptable under existing cultural and religious mores, which offers improved reliability without the need for intervention by medical professionals.

To address some of the foregoing issues, a more reliable procedure, known as the sympto-thermal method, involves a subjective evaluation of both basal body temperature and cervical mucus to determine the fertile period. However, this method requires intensive user training, and relatively high variability of results and failure rates were and are still unavoidable.

In this procedure, changes in cervical mucus are combined with basal body temperature ("BBT") to identify the onset and end of the fertile period. There are several disadvantages with this approach, among them being the need for immobility before taking the BBT, daily monitoring of the cervix and vagina, and subjective interpretation of vaginal mucus quality and of the BBT trend. The technique is difficult to learn, with one to six months of careful training and supervision being required to attain proficiency. Another relatively serious problem with this particular methodology is the variation of the relation between the basal body temperature and the peak mucus symptom, known as spinnbarkheit. Furthermore, BBT correlates with ovulation in only about 70% of female cycles, since monophasic (non-indicative) BBT patterns are frequently seen in ovulatory cycles. Thus, when use of this methodology has been attempted for birth control, failure rates of up to 34% have been recorded. Although computerized interpretation of data is now available for the sympto-thermal method, for example as disclosed in U.S. Pat. No. 4,151,831, issued May 1, 1979, to Lester, the disadvantages obviously inherent in the physiological parameters used in the method are still limiting factors.

Other methods well known in the art are more invasive of the body, but can be good indicators of the time of ovulation. The identification of a preovulatory rise in estrogens followed by a peak in luteinizing hormone (LH) concentration, as determined by radioimmunoassay, is a good indication of imminent ovulation. Frequently, several samples of blood, drawn at mid-cycle, are analyzed for luteinizing hormone concentration. These techniques are expensive, involve invasive drawing of blood from the subject, and require several visits to a hospital or medical laboratory having the appropriate analytical facilities.

The process of ovulation has also been monitored and detected using ultrasonography. However, this procedure is time-consuming and expensive for the subject, as daily visits to a center equipped with the sophisticated instrumentation used for the procedure are necessary. Several scans are required to pinpoint ovulation by observing follicular development and subsequent ovum release. While accurate identification of ovulation is possible with this technique, it is of little value as a self-monitoring method for purposes of enhancing or reducing fertility.

Several methods of predicting ovulation based on biochemical changes in various body fluids such as vaginal secretions, saliva, or urine have been proposed. The major drawback of such methods is the significant variation in the component being measured between individuals. For example, in one method, where the lactic acid concentration of vaginal secretions was proposed as an indicator of impending ovulation, the variability of its concentration between individuals was as great as one thousand percent. See U.S. Pat. No. 4,010,738, issued Mar. 8, 1977, to Preti et al.

As a practical matter, it is generally believed at the present time to be impossible to design a chemical indicator system that is applicable to all women. One example of such a problem is related to the alkaline phosphate levels of saliva that, although appearing to be predictive of ovulation, show such variations among individuals that any chemical means of monitoring for its changes requires that tests be individually calibrated to each user. Methods based on analysis of urine for steroid hormones or their derivatives are subject to the same problem.

U.S. Pat. Nos. 4,685,471, 4,770,186 and 4,836,216, commonly assigned herewith, describe methods and apparatus for predicting ovulation in a human female subject which overcome many of the shortfalls and limitations of the methods described above. In the performance of this method, the onset of menstruation of the subject is noted, and daily determinations are made of the electrical resistivity of the subject's saliva, beginning not more than five days following beginning of menstruation. The onset of ovulation is determined as a function of a peak resistivity measurement following onset of menstruation, which peak is followed by a nadir and subsequent sharp increase in saliva electrical resistivity measurement. Vaginal resistivity measurements may be made to confirm ovulation. A probe is used for the resistivity measurement. Although the methods and apparatus described in these patents are greatly advantageous over all of the aforedescribed methodologies, nevertheless the need exists for improvement, in order to provide more accurate results and increase the subject's compliance with the proper procedures for performing the methods, and also to increase acceptance of the methods by philosophical and religious groups. It is these latter issues that the improved apparatus and methods of the present invention seek to address.

SUMMARY OF THE INVENTION

In accordance with the present invention, improvements in the accuracy and reproducibility of the results of the resistivity measurements performed in accordance with the methods disclosed in commonly assigned U.S. Pat. Nos. 4,685,471, 4,770,186 and 4,836,216, and substantial automation of the methods, enabling advantageous results by comparison with the prior systems and methods described in these patents, is made possible through the utilization of novel, improved algorithms employed in the diagnostic system and methods for predicting and confirming ovulation based on the resistivity measurements taken. In addition, through extensive continued research involving the use of the method and apparatus described in these commonly assigned patents, numerous additional and greatly advantageous applications for the method and apparatus have been discovered. These improvements and discoveries have enabled the invention described and claimed herein to be greatly improved over all of the prior systems and methods, and to have applications for determining and/or monitoring various physiological conditions in female mammals, other than providing merely the prediction and confirmation of ovulation.

Accordingly, in accordance with the present invention, an improved diagnostic system is provided comprising:

(a) a read only memory means for storing a diagnostic program for determining the fertility state of the female subject from salivary and vaginal resistance data values, (b) a random access memory means for storing temporary data values;

(c) a non-volatile memory means for storing daily data values;

(d) a display means for displaying characters representing the fertility state;

(e) a microprocessor means for controlling the processing of data in accordance with said diagnostic program, said microprocessor means being connected to read only memory means, said random access memory means, said nonvolatile memory means, and said display means;

(f) a sensing means for sensing the resistance of an electrical path along the tongue or in the vagina of the female subject and outputting analog signals, (g) a conversion means for converting said analog signals to digital signals;

(h) an input means for enabling the input of data by the female subject; and (i) a first interface means connected to said input means and said analog-to-digital conversion means for enabling the input of digital signals representing a current daily data value to said microprocessor means, and wherein said diagnostic program comprises algorithms for the recognition of predetermined patterns of data values, said algorithms being applied to said current daily data value and said stored daily data values by said microprocessor means, said microprocessor means controlling said display means to display characters representing one of several fertility states of said subject in response to recognition of a corresponding one of said predetermined patterns, the improvement wherein said algorithms are capable of determining variables that can be used to define the beginning of the fertile cycle of the mammal, the end of the fertile cycle of the mammal and the most fertile day of the mammal.

There is also provided by the invention, an improved ovulation prediction apparatus based on that disclosed and claimed in the aforementioned commonly-assigned patents, and having a housing which contains electronic means for processing the above-described information, and also preferably including means associated therewith which serve as one or more sensors to transmit information to the means for processing information, and a means for substantially automatically indicating the presence of a viable egg, including an audible component and a visual component. The means for processing the information includes at least one microprocessor-controlled circuit. The information is processed and compared with data associated with the presence of a viable egg, such that if a viable egg is empirically indicated as being present, then the means for indicating the presence of a viable egg will indicate such presence.

Accordingly, it is a primary object of the present invention to provide an improved electronic ovulation prediction apparatus that is simple and convenient to use and which results in a quick and effective determination and confirmation of whether a viable egg is present.

It is a further object of the present invention to provide novel, additional, and greatly advantageous uses and applications which are enabled by the improved ovulation prediction apparatus and the method for utilizing it of the present invention, which have been discovered to be outside the field of ovulation prediction. It is to be understood and appreciated that these discoveries in accordance with the invention are only those that are illustrative of the many additional potential applications of the apparatus and method that may be envisioned by one of ordinary skill in the art, and thus are not in any way intended to be limiting of the scope of the invention. Accordingly, other objects and advantages of the invention will be apparent to those skilled in the art from the following detailed description, together with the appended claims.

DETAILED DESCRIPTION OF THE INVENTION

Reference to Existing Patents

The improvements provided by the present invention have been specifically made to the devices and methods disclosed in the following United States Patents, all commonly assigned herewith. All of these patents are expressly incorporated herein by reference:

U.S. Pat. No. 4,685,471—Method and Apparatus for Predicting and Detecting the Onset of Ovulation, issued Aug. 11, 1987

U.S. Pat. No. 4,770,186—Method and Apparatus for Predicting and Detecting the Onset of Ovulation, issued Sep. 13, 1988

U.S. Pat. No. 4,836,216—Method for Predicting Optimum of Insemination, issued Jun. 6, 1989

According to the present invention, the apparatus and methods disclosed in the foregoing U.S. Pat. Nos. 4,685, 471, 4,770,186 and 4,836,216, are greatly and advantageously improved by the use of the discoveries and features of the invention, which are now described in more detail in the following text. These improvements, and novel applications of the thereby improved apparatus and methods of the invention, together with their advantages, will be readily apparent to one skilled in the art by reference to the above-described patent and the preferred embodiments described herein.

One particularly advantageous aspect of the present invention is that it greatly simplifies the testing process and results in numerous economies for the users. For instance, unlike many alternative systems, the invention does not require a prolonged period of time to perform the analysis, nor are comparative tests required to get extremely accurate readings. Moreover, the improvement in the algorithm used in the practice of the method of the invention, by comparison with the methodologies of the above-described prior patents, enables the performance of multiple confirming tests simultaneously, thus providing substantial automation. In this manner, the invention can immediately provide information on the positive or negative status of a women's fertility and the condition of her reproductive health.

The improvements provided by the invention enable its use without extensive training. Furthermore, the device and its associated processes can be associated with a visual reference system designed to be language independent so that it can be used anywhere in the world, and may be adapted for use in areas where the user may in fact be illiterate. Also, because the invention can determine and inform the user when positive ovulation has occurred, it can help a woman prevent or postpone pregnancy, or assist a woman in becoming pregnant naturally, as desired. The invention has furthermore been found to be accurate during any reproductive situation, including breastfeeding, premenopause, and after the discontinuation of medication including, without limitation, contraceptive pills, and during times of illness or stress. For women having difficulty becoming pregnant the invention can help identify many specific infertility problems relating to reproductive health.

The invention can support or reduce the use of other contraceptives and support or reduce the use of other ovulation test methods. Thus, it is apparent that the apparatus provided by the invention may also be used as a stand-alone birth control device or reproductive health tool. The invention can therefore also help to eliminate the harmful side effects of contraceptive devices and chemicals. Further, the visual display and data handling and storage capabilities of the improved apparatus of the invention provides information directly to the woman or health care providers assisting her, thus providing self-confidence, independence and security by obtaining knowledge as to exactly when she can or cannot become pregnant.

The improvements provided by the invention can also satisfy curiosity about the natural body processes of a woman, and helps the user identify cyclic emotional swings, thereby enabling treatment of premenstrual discomfort, especially in the case of identifying proper treatment with estrogen versus progesterone. Also, in assisting reproductive health, the invention allows the user to become immediately aware of abnormalities that may indicate infections, hormonal abnormalities, or other changes in the user's physiological status.

The invention can also assist in reducing costs, and help remove potential barriers from users who are financially unable to afford or gain access to more expensive prior art tests or equipment. Because of the improvements made to the present apparatus, which enable its high accuracy, ease of use and manufacturing, together with the fact that it, by comparison with many prior art methodologies, honors religious or personal convictions prohibiting artificial contraceptives or the use of blood or urine, it is expected that the present invention will be endorsed by religious authorities and world governments, and will be widely distributed to support population awareness and reproductive health for both men and women.

An extensive research project was undertaken in the development of the improved apparatus and method of the present invention, which particularly explored the physiological bases for the major signals produced during use of the invention as a diagnostic system. This research has shown the apparatus of the invention, improved as described herein, to be a beneficial instrument for screening for several common ovulatory disorders. Data collected in the normal course of infertility treatment can also be interpreted to alert the physician or consumer to the need for additional testing to confirm or rule out the identified problem. The apparatus provides precise signals of the onset of the preovulatory rise in estrogens, as well as the time of ovulation. When used as a screen for ovulatory disorders, the apparatus would allow earlier and more reliable direction for the diagnostic workup in infertility patients than is currently in use. Accordingly, application of the diagnostic system provided by the invention in suggesting the existence and nature of an ovulatory disorder, can increase the cost- and time-effectiveness of infertility treatment. While the inventive apparatus and method probably would not be used as the only means of identifying an ovulatory disorder, under the guidance of a skilled medical practitioner their potential for such use will be apparent to one skilled in the art. This use can be as a screen for luteal phase defect, in which a Peak reading, vaginal low, and Vaginal Rise are seen. Vaginal readings, however, are not sustained at the normal increased level during the weeks immediately following ovulation (luteal phase). Lowered readings during this portion of the cycle correlate strongly with luteal phase defect, which is related to increased estrogen and/or decreased progesterone during this part of the cycle. Endometrial biopsy and/or serum progesterone assays can be performed as early as the first cycle in which this pattern is seen to substantiate or rule out the diagnosis once the indication is observed.

A screen for luteinized unruptured follicle is another use in which the diagnostic system of the present invention, improved over the prior devices described, can be advantageously employed. This disorder is characterized by a normal pattern in the oral readings taken from the apparatus, as well as normal vaginal readings, during the follicular phase, but with a failure of the vaginal readings to show the characteristic sharp rise five to seven days after the observed peak in the oral readings. Ultrasound and/or blood tests can then be used to confirm the indication. While many women have an occasional cycle with a luteinized unruptured follicle, the occurrence of one or two such cycles as indicated by readings taken from the apparatus of the invention should alert the physician to this potential effect on the patient's fertility. Monitoring the follicle with ultrasound timed by the readings can provide a sound basis for appropriate therapy.

A screen for atresia or interruption of follicle development after follicle selection is also possible by the practice of the method of the invention. An absence of decreasing vaginal readings for more than three days after the peak of oral readings indicates that, although a follicle was selected, it did not develop normally or reach maturity. The possibility of this disorder can be identified early enough in a cycle to allow for treatment in that same cycle. Alternatively, it can be confirmed or ruled out by ultrasound and/or serum progesterone assay in the concurrent cycle and treatment initiated in the succeeding cycle. This pattern of diagnosis could shorten the diagnostic process by as much as four cycles.

The improved apparatus and methods of the invention, which form the improved diagnostic system provided, can also be employed to identify women with probable anovulation. When a peak reading is not seen and oral and vaginal readings follow a roughly parallel pattern, failure of follicle selection (anovulation) is suggested. Presence of this pattern in two or three successive cycles indicates a need for additional diagnostic testing to confirm the indication and to develop an appropriate treatment.

It has further been found that the improved diagnostic system of the invention can be employed as a screen for Stein-Leventhal Syndrome, or Polycystic Ovary Syndrome. A characteristic pattern from readings taken from the apparatus of the invention indicating Polycystic Ovary Syndrome ("PCOS") has been observed. Readings indicative of this syndrome show multiple peaks in the oral readings that have the mathematical character of a normal Peak, but lack the clear rise in vaginal readings. In many cases of this syndrome, this pattern is seen to recur several times during a cycle, often followed by a normal vaginal reading pattern indicating ovulation, and by menstruation approximately 14 days later. Patients with PCOS usually present with observable physiological characteristics such as extraordinarily long menstrual cycles, obesity or overweight, and unusual patterns of facial hair. However, these characteristics alone are not sufficient to support the diagnosis. Addition of information from the readings can justify the additional testing and therapy needed to treat the syndrome.

Timely treatment of PCOS is essential in cases of resulting infertility. However, even when infertility is not a concern, diagnosis and treatment are beneficial to the patient. Most women with this syndrome, unless they are concerned with infertility, suffer the symptoms for long periods of time or undertake self-treatment for such symptoms as overweight and/or obesity. Identifying the hormonal basis of their condition and providing appropriate therapy would provide direct benefit to the patient as well as cost-effective, proactive care.

A June 2000 report in the journal *Fertility and Sterility* indicates an important role for insulin sensitivity in PCOS. Treatment of 39 women with PCOS with a common insulin-sensitizing drug (metformin) yielded positive results. A complex set of blood hormone measurements was used to assess the outcome. In a clinical setting, if metformin therapy were to be used, data from the improved diagnostic system of the invention could be a simple "bottom-line" monitor for the normalization of ovulatory cycles.

The diagnostic system of the present invention can also be advantageous in assessing cycles in women without ovulatory disorders. Currently understood potential applications of the invention for women who do not suffer from an ovulatory disorder but can benefit from more detailed knowledge of the hormone patterns include:

i. Defining the follicular and luteal phases of the menstrual cycle; this application is useful for scheduling tests such as the mid-luteal phase endometrial biopsy and/or progesterone assay as well as other tests that must be performed at a particular stage of the cycle.

ii. Identifying ovulatory and non-ovulatory cycles during peri-menopause; there is wide variation among individuals as to the age of onset of menopause. Readings from the invention, when coordinated with awareness of their relationship to the production of pituitary, adrenal, and gonadotropic hormones, can alert a woman and her doctor to these pre-symptomatic changes in her body. Use of the readings for this purpose can be particularly useful for women whose age does not suggest the likelihood of menopause, but who may be experiencing premature menopause. Similarly, the readings can be expected to signal the return of fertility in nursing mothers.

iii. Characterizing Pre-menstrual Syndrome (PMS); studies in connection with use of the invention suggest that the diagnostic system provided by the invention can identify those instances of PMS that can be expected to respond well to specific hormone therapies such as progesterone. The invention can also be useful in identifying individuals whose pre-menstrual discomfort cannot be attributed to a progesterone deficiency.

It will be apparent to those skilled in the art that the improved diagnostic system provided by the invention can be utilized as a method for birth control, and although currently not approved by government regulatory authorities for such use, it could readily be implemented as such. The system, improved over the prior systems as herein described, accurately defines the fertile period of women, such that abstinence through this fertile period would be effective as a method for contraception. Because it has been found that the system in accordance with the invention is at least 98% accurate in determining this fertile period, its effectiveness compares positively to that of popular methods of contraception.

A study conducted at The Baylor College of Medicine confirmed the present inventors' preliminary conclusions that the use of data from the system hereof is effective and desirable for the avoidance of conception by abstinence or by periodic use of barrier methods during the fertile phase of a woman's cycle. The authors of the study devised an algorithm for using the present invention for this purpose, which shortened the period of abstinence by four days, to 9.2 days by comparison with the 13.4 days required by the widely used symptothermal method (which requires daily examination of vaginal mucus and daily recording of BBT).

In another study, at Providence Hospital in Holyoke, Mass., experienced users of another form of the symptothermal method used the diagnostic system, which has been improved by the invention as set forth herein, in parallel with their standard method. In 30 cycles in this study, the period of abstinence defined by the diagnostic system was 10.2 days, and by the symptothermal method was 12.2 days. The study author concluded that " . . . the [diagnostic system] method is a promising first step toward a method of ovulation prediction that can really help some of our clients, especially those who are breast feeding and cycling, those who are premenopausal, those who do not have a biphasic BBT chart, and all the others in situations where natural family planning is difficult to learn and difficult to practice."

An examination of another 153 cycles using data generated by the improved diagnostic system hereof and serum LH data, from the point of view of defining the period of abstinence, yielded a mean duration of presumed fertility of 9.9 days, while no signals from the inventive apparatus fell with the period of fertility, i.e., there would have been no occasion of unintended conception using the method of the present invention.

The present invention has been developed keeping in mind such potential users of the method for this purpose. Many couples are deeply committed to using information about the woman's fertility cycle as a means of avoiding conception, i.e., "Natural Family Planning" (NFP). Many of these couples are motivated by religious commitment; however, more and more important are concerns of couples about using the other available methods, from a health standpoint. It has been observed that most of these individuals find birth control pill side effects undesirable, barrier methods distasteful, and other NFP methods too demanding or insufficiently reliable.

Summary of Clinical Results

Clinical results based on the use of the improved diagnostic system of the invention are identified in the previous section and are based on The National Institutes of Health ("NIH") Phase I and Phase II studies of a method and device of the invention that were conducted at the University of Colorado Health Science Center in Denver, Colo. At the completion of Phase I, the authors reported extensive field research, which forms one of the bases for the additional applications of the improved diagnostic system of the invention set forth herein, and showed, specifically, that the improvements made provide an effective method for detecting ovulatory disorders.

The Phase II study of the NIH Report incorporated the data of hundreds of women's cycles to determine and prove the improved diagnostic system is an accurate and viable tool for predicting and detecting the time of ovulation in women. An additional conclusion of the investigation was the determination of the advantages of the automated algorithm, necessary to interpret the data signals from the apparatus in the performance of the method, as integrated into a microprocessor-based preferred embodiment of the inventive device. This algorithm, and its manifestation into a working device, are described later in this Specification and are crucial aspects of the present invention.

It will be apparent to those of ordinary skill in the technical field to which this invention pertains, that because the ovulatory cycle in common breeding mammals is similar to that of humans, the diagnostic system provided by the present invention can be, and has been, used successfully in the veterinary field to predict ovulation in these and other animals. Further, the invention has been used successfully in the veterinary field to determine the onset of mastitis in animals earlier than any other method presently known. This application is important to dairy operators and to the health of the general public, as one dairy cow infected with mastitis can contaminate all milk within the same batch being processed at the processing facility.

Thus, as has been described above, the present invention provides specific improvements to the prior apparatus and methods described in the above-listed, commonly assigned US patents. These improvements, as well as the advantages of the improvements provided by the invention over the apparatus and methods of the prior art, as aforedescribed, will now be described in greater detail. The preferred embodiments of the invention which incorporate these improvements, which make possible not only the automation features and the greatly improved ease of use of the apparatus and methods provided by the invention for predicting and confirming ovulation in mammals, as described previously have also been found, unexpectedly, to enable the invention to be employed in many fields and applications in addition to the prediction and confirmation of ovulation, such as in the diagnosis, prevention and treatment of various physiological and disease states.

Accordingly, in one aspect the invention provides an improved diagnostic system for determining the onset of ovulation in female mammals, wherein the diagnostic system comprises:

(a) a read only memory means for storing a diagnostic program for determining the fertility state of the mammal from salivary and vaginal resistance data values, (b) a random access memory means for storing temporary data values;

(c) a non-volatile memory means for storing daily data values;

(d) a display means for displaying characters representing the fertility state;

(e) a microprocessor means for controlling the processing of data in accordance with said diagnostic program, said microprocessor means being connected to read only memory means, said random access memory means, said nonvolatile memory means, and said display means;

(f) a sensing means for sensing the resistance of an electrical path along the tongue or in the vagina of the female mammal and outputting analog signals, (g) a conversion means for converting said analog signals to digital signals;

(h) an input means for enabling the input of data by the female subject; and (i) a first interface means connected to said input means and said analog-to-digital conversion means for enabling the input of digital signals representing a current daily data value to said microprocessor means, and said diagnostic program comprising algorithms for the recognition of predetermined patterns of data values, said algorithms being applied to said current daily data value and said stored daily data values by said microprocessor means, said microprocessor means controlling said display means to display characters representing one of several fertility states of said subject in response to recognition of a corresponding one of said predetermined patterns; and the improvement wherein said algorithms are capable of the substantially automated determination of variables that can be used to define the beginning of the fertile cycle of the mammal, the end of the fertile cycle of the mammal and the most fertile day of the mammal.

The improvement provided by the invention will now be described in terms of preferred embodiments of the algorithms utilized. These novel algorithms were developed, following extensive research, as improvements to be incorporated in the prior apparatus and methods described in the foregoing commonly-assigned patents, and are based on determining the few key variables that can be used to define the beginning of the fertile cycle (selection of a dominant follicle), the end of the fertile cycle (the occurrence of ovulation) and the most fertile day of a woman. The definitions of these variables are as follows, and they are referred to in the remainder of this Specification, with reference to human female subjects, as:

1. Peak—a particular peak in the oral readings, which signifies the onset of the fertile phase of the cycle
2. Start Day—the start day of the cycle
3. Vaginal Low—the nadir of the vaginal readings, which identifies the day before ovulation
4. Vaginal Rise—a particular rise in vaginal readings, which signifies the occurrence of ovulation The identification of the value and occurrence of these variables enables the improvements provided by the novel algorithm of the invention, when used in the improved diagnostic system of the invention, to both predict and confirm ovulation in women, by comparison with prior methodologies that are only predictive. The determination of the variables is identified in the following detailed description of an especially preferred embodiment of an algorithm of the invention:

1. Peak

The Peak is a high oral reading, followed by two, consecutive, once daily, morning oral readings which are lower than the high reading; where the first reading is lower by >2%, the second is lower by >1%

AND

The sum of the percentage change between the high readings and the first day, plus the percentage change between the high reading and the second day is >=10%.

IF

This high reading occurs on or after the start day for the particular cycle and before the start day plus 7.

2. Start Day

The Start Day is defined as either:

day 3 of administration of Clomiphene citrate (Clomid or Serophene)

OR if cycle length>=30; then start day cycle length−22

OR if cycle length<=25; then start day=cycle day 4

OTHERWISE start day=cycle day 5

3. Start of Vaginal Readings

Vaginal readings are to be started on the first day after the start day on which the oral reading drops by 2% or more

OR on cycle day 8; whichever is earlier.

4. Minimum Vaginal Reading

The Minimum Vaginal Reading is defined as the current day's vaginal readings

IF it is not >=12% higher than the previous day's reading

AND it occurs on or after day 4 after oral peak when oral peak is before cycle day 11

OR it occurs on or after day 3 after oral peak when oral peak is on or after cycle day 11.

5. Vaginal Rise

The day of Vaginal Rise is the first rise in vaginal readings which is >=12% higher than the Minimum Vaginal Reading

IF all vaginal readings on or before the day of Peak plus 8, remain higher than the Minimum Vaginal Reading

OTHERWISE the vaginal reading which is lower than the previous Minimum Vaginal Reading will be considered to be the new Minimum Vaginal Reading, and data will be observed for a second valid rise immediately after by the method described above

PROVIDED THAT no Vaginal Rise can occur after the day Peak plus 11

AND PROVIDED THAT no second Vaginal Rise can occur after day Peak plus 9

If no Vaginal Rise has been seen before day Peak+12, the originally identified Peak is ignored, and a new Peak is looked for in the period: old Peak+1 up to and including start day+11.

In the use of the diagnostic system of the invention, interpretation of the data can be made with reference to the following chart, based on statistical regression analysis of results produced by the NIH studies described herein, and which identifies the time of peak fertility, by the cycle day:

| Peak | Peak Fertility |
| --- | --- |
| 4 or 5 | 12 |
| 6 or 7 | 13 |

-continued

| Peak | Peak Fertility |
|---|---|
| 8 or 9 | 14 |
| 10 or 11 | 15 |
| 12 or 13 | 16 |

2. Automation Menu Hierarchy

An especially preferred embodiment of the method of the invention involves the use of the algorithm of the invention, as previously described, in largely conventional microprocessor control circuitry and associated electronics, such as that described in the foregoing commonly-assigned patents herein incorporated by reference, to produce an automated device, the display of which has the following key menus:

Main Menu
1. User Setup
2. Take Readings
3. Calculate Fertility
4. Review/Download Readings
5. Set Date and Time
1. User Setup
   1.1. "Set Date and Time?", if yes, goto 5.1
   1.2. "Set 1$^{st}$ day of Cycle?", if yes goto 1.2.1
      1.2.1. if yes, "Enter first menses date"
      1.2.2. validate (1–31), cday=1
   1.3. "Set Cycle Length?"
      1.3.1. if yes, "Enter avg. cycle length"
      1.3.2. validate (1–40), cycle_ length
   1.4. "Medication Used?"
      1.4.1. if yes, "Enter Med. cycle day"
      1.4.2. validate (1–40), clomid
2. Take Readings
   2.1. Check if Date and Time Set
      2.1.1 Date Set? If no, goto 5.1
      2.1.2 Time Set? If no, goto 5.2
   2.2 Take Oral Reading
      2.2.1.—"Connect Oral Sensor"
      2.2.2.—"Sensor Ready?"
      2.2.3.—Take Oral reading
      2.2.4.—if read_vr=true, remind for VR
   2.3. Take Vaginal Reading
      2.3.1.—If read_vr=true, then
      2.3.2.—"Connect Vaginal Sensor"
      2.3.3.—"Sensor Ready?"
      2.3.4.—Take Vaginal Reading
3. Calculate Fertility
   3.1.—Check if enough data, if no, error, else continue
      3.1.1.—if cday<5 OR prev_cycle=false, then goto 3.1.2
      3.1.2.—display error message, "insufficient data"
   3.2.—Calculate Fertility (run algorithm modules)
      3.2.1.—determine start day
      3.2.2.—find Peak
      3.2.3.—find vr_min
      3.2.4.—find vr_rise
      3.2.5.—calculate fertility
4. Review/Download Readings
   4.1.—Review Oral readings
      4.1.1.—previous reading
      4.1.2.—next reading
   4.2.—Review Vaginal readings
      4.2.1.—previous reading
      4.2.2.—next reading
   4.3.—Download readings
      4.3.1.—Connect Infrared Receiver
      4.3.2.—"Open download software"
      4.3.3.—Download readings
   4.4.—Delete Readings
      4.4.1.—Verify, if yes, 4.4.2.
      4.4.2.—Delete all readings
5. Set Date and Time
   5.1.—Set Date
      5.1.1.—Set Day
      5.1.2.—Set Month
      5.1.3.—Set Year
   5.2.—Set Time
      5.2.1.—Set Hour
      5.2.2.—Set Minute
      5.2.3.—Set am/pm
6. Contact Manufacturer
   6.1.—Contact Manufacturer
      6.1.1.—Display manufacturer phone number and website address 4. Description of Companion Software for Personal Computer Because in a particularly preferred embodiment, the diagnostic system of the invention is incorporated in a handheld device, such as that described in detail in the herein incorporated-by-reference disclosures of U.S. Pat. Nos. 4,685,471, 4,770,186 and 4,836,216, the improved system of the invention can be further enhanced by the use of companion software to provide functionality not possible in the hand-held apparatus. The companion software, which can be run on a conventional personal computer, can provide the following functions:

a. Download Data

This option allows the user to download, via the infrared signal of the apparatus, their particular oral and vaginal readings. In a typical case where three months of accumulated data are stored in the memory of the device, after that time, if a user wants to keep a record of past readings they would use the download data option of the companion software.

b. Share Data

In many cases, the user has the need to share the oral and vaginal readings with others, especially their physician, the manufacturer or support groups. The companion software enables the user to make their personal data available to authorized recipients, for example via the Internet or a standard media device (floppy disk, CD, etc.).

c. Graph Data

Interpretation of the results of the readings is easier for some individuals when it is presented in a graphical format. This option of the companion software allows the user to generate a graph of their oral and vaginal readings. The peaks and nadirs in the readings can then be easily identified.

d. Store Data

The companion software is not practically limited in the amount of readings it can store, since the associated personal computer can be used for storage on such media as floppy disks, etc. This feature of the software allows the user on long-term basis to keep a record of past readings and compare fertility status at various periods.

It is also to be appreciated that the improvements which are incorporated into the present invention are not limited to the algorithms as previously described, but that the improved diagnostic system incorporates a number of precision components (tolerance <1%) in key processing points to increase the accuracy and reliability of the readings over the previously known apparatus and methods, and various other improvements which enhance functionality, all of which features and enhancements will be understood by those skilled in the art as being desirable, but not critical, to the functioning of the invention as herein disclosed and claimed. Examples of preferred embodiments of such features, which are improvements made in accordance with generally recognized, conventional engineering practice at the present time, are:

Digital Display:

The interface to the diagnostic system is based on an expanded, commercially available, digital Liquid Crystal Diode ("LCD") display, which displays the characters with greater size and accuracy. This provides for greater user-friendliness and allows the system to be used by those who are visually impaired.

Circuitry Design:

The circuitry design for the new diagnostic system, while employing largely conventional design techniques, has been redesigned to take advantage of the latest, computerized CAD/CAM methods, which provide a more streamlined and efficient electrical processing of the user data. This has enabled significant improvements in board layout and design, especially with regard to the manual layout methods used in connection with the prior devices, which in turn enhance the manufacturability and reduce the costs of manufacture of the hardware used.

Printed Circuit Board:

The circuit board of the system has been implemented using conventionally available multi-layer photo-filament boards and microcomputer based photo imaging. This enables the components to be placed in relation to each other to minimize electrical interference from each component and increase the accuracy and reliability of the readings.

Microprocessor

The improved system of the invention incorporates several conventional but state-of-the-art microprocessor and integrated circuit chips that add to the accuracy and speed of the instrument.

Sensors

The improved system of the invention, as in the prior systems, contains two sensors, one for oral readings, and preferably one for vaginal readings. The oral sensor has been improved by redesigning the sensor surface area to provide better contact with the saliva and provide the user with greater consistency and accuracy in the oral readings than has been possible in the use of the prior art devices. The vaginal sensor has been improved to eliminate the need for a separate cable attaching the sensor to the main unit. This eliminates the need for the user to secure the cable and provides more accuracy and reliability in the vaginal readings as well as added convenience to the consumer.

Manufacturing:

In manufacturing of the improved diagnostic system of the invention, a commercially available, high-integration microcontroller with built-in time codes, ROM and improved firmware capabilities is used, together with an improved microprocessor. As described above, an enhanced, substantially automated capability is provided by the algorithm for determining peak fertility based on the results of the readings. In the manufacturing process, the algorithm is developed and compiled for implementation into the microprocessor contained in the device, in a manner well known to those skilled in the art. This enables the device to substantially automatically interpret the data, thereby providing the user with almost immediate and clear results.

It will be apparent to those skilled in the art that the improved diagnostic system of the invention is not to be limited by the foregoing description of preferred embodiments, and that any such limitations are only to be defined by the appended claims.

What is claimed is:

1. An improved diagnostic system for determining or monitoring a physiological condition in a mammal, said diagnostic system comprising:
   (a) a read only memory means for storing a diagnostic program for determining the fertility state of the mammal from salivary and vaginal resistance data values,
   (b) a random access memory means for storing temporary data values;
   (c) a non-volatile memory means for storing daily data values;
   (d) a display means for displaying characters representing the fertility state;
   (e) a microprocessor means for controlling the processing of data in accordance with said diagnostic program, said microprocessor means being connected to read only memory means, said random access memory means, said nonvolatile memory means, and said display means;
   (f) a sensing means for sensing the resistance of an electrical path along the tongue or in the vagina of the female mammal and outputting analog signals,
   (g) a conversion means for converting said analog signals to digital signals;
   (h) an input means for enabling the input of data; and
   (i) a first interface means connected to said input means and said analog-to-digital conversion means for enabling the input of digital signals representing a current daily data value to said microprocessor means,
   and said diagnostic program comprising algorithms for the recognition of predetermined patterns of data values, said algorithms being applied to said current daily data value and said stored daily data values by said microprocessor means, said microprocessor means controlling said display means to display characters representing one of several fertility states of said subject in response to recognition of a corresponding one of said predetermined patterns;
   the improvement wherein said algorithms are capable of the automated determination of variables that can be used to define the beginning of the fertile cycle of the mammal, the end of the fertile cycle of the mammal and the most fertile day of the mammal.

2. The improved diagnostic system as defined in claim 1, wherein said algorithms are capable of the substantially automated determination of first, second, and third patterns of data values, said first pattern being that the current daily data value is less than the previous daily data value by a first predetermined amount, said second pattern being that the current daily data value is greater than the previous daily data value by a second predetermined amount and the previous daily data value is less than the next preceding daily data value by a third predetermined amount, and said third pattern being that the current daily data value is greater than the previous daily data value by a fourth predetermined amount.

3. The improved diagnostic system as defined in claim 1, further comprising means connected to said microprocessor means for converting parallel data signals to synchronous serial signals for forming a communications link with an external device.

4. The improved diagnostic system as defined in claim 1, further comprising a real-time clocking means operatively connected to said microprocessor means by way of a second interfacing means.

5. The improved diagnostic system as defined in claim 1, further comprising a decoding means connected to said microprocessor means for decoding control and address signals output by said microprocessor means.

6. In a diagnostic system for determining and monitoring a physiological condition in a female subject, said system comprising:
   (a) a first probe means for outputting data signals representing the resistance value of an electrical path along the surface of a first body part of said female subject;
   (b) a second probe means for outputting data signals representing the resistance value of an electrical path along the surface of a second body part of said female subject;
   (c) an electronic data processing means having a port for interchangeably receiving either of said probe means, said data processing means including
      (i) means for applying a first pattern detection algorithm to said data signals in response to recognition of said first probe means,
      (ii) means for applying a second pattern detection algorithm to said data signals in response to recognition of said second probe means,
      (iii) means for outputting first and second control signals in response to detection of data signals representing first and second patterns of successive resistance values, respectively, and
   (d) a display means connected to receive the output of said data processing means and to display characters representing first or second fertility states of said female subject, respectively, in response to receipt of said first or second control signals; the improvement comprising said algorithms being capable of substantially automated determination of variables that can be used to define the beginning of the fertile cycle of the mammal, the end of the fertile cycle of the mammal and the most fertile day of the mammal.

7. The improved diagnostic system as defined in claim 1, wherein the physiological condition is the onset of ovulation.

8. The improved diagnostic system as defined in claim 1, wherein the physiological condition is luteal phase defect.

9. The improved diagnostic system as defined in claim 1, wherein the physiological condition is luteinized unruptured follicle.

10. The improved diagnostic system as defined in claim 1, wherein the physiological condition is atresia.

11. The improved diagnostic system as defined in claim 1, wherein the physiological condition is anovulation.

12. The improved diagnostic system as defined in claim 1, wherein the physiological condition is Polycystic Ovary Syndrome.

13. The improved diagnostic system as defined in claim 1 or claim 6, wherein the physiological condition is an ovulatory disorder.

14. The improved diagnostic system as defined in claim 1 or claim 6, wherein the physiological condition is a non-ovulatory disorder.

15. In a method of diagnosing the existence of a physiological condition in a subject mammal, which method comprises the steps of making daily determinations of the electrical resistivity of the subjects saliva beginning not more than five days following the onset of menstruation by applying a first sensor for forming analog data signals representing salivary electrical resistivity, converting said analog data signals to digital data signals, processing said digital data signals over a predetermined time to obtain a digital data signal representing the current daily value of the salivary electrical resistivity, storing said daily salivary electrical resistivity values in memory, applying a first algorithm for pattern recognition to the stored values, generating a first recognition signal in response to the first occurrence of the current daily value being less than the previous daily value by more than a predetermined significant amount, displaying a signal indicating a high probability of conception in response to generation of said first recognition signal, digitally displaying said current value resulting from said processing step, applying a second algorithm for pattern recognition to the stored values, and generating a second recognition signal in response to the occurrence of a predetermined relation between three consecutive daily values, making daily determinations of the electrical resistivity of the subject's vaginal mucus beginning after the generation of said first recognition signal by applying a second sensor in the subject's vagina for forming analog data signals representing vaginal electrical resistivity, converting said analog data signals to digital data signals, processing said digital data signals over a predetermined time to obtain a digital data signal representing the current daily value of the vaginal electrical resistivity, storing said daily vaginal electrical resistivity values in memory, applying a third algorithm for pattern recognition to the stored values, generating a third recognition signal in response to the first occurrence of the current daily value being greater than the previous daily value by more than a predetermined significant amount, and displaying a signal indicating a low probability of conception one day after the generation of said second recognition signal, the improvement wherein said algorithms are capable of substantially automated determination of variables that can be used to define the beginning of the fertile cycle of the mammal, the end of the fertile cycle of the mammal and the most fertile day of the mammal.

16. The method of claim 15, wherein the physiological condition is the onset of ovulation.

17. The method of claim 15, wherein the physiological condition is luteal phase defect.

18. The method of claim 15, wherein the physiological condition is luteinized unruptured follicle.

19. The method of claim 15, wherein the physiological condition is atresia.

20. The method of claim 15, wherein the physiological condition is anovulation.

21. The method of claim 15, wherein the physiological condition is Polycystic Ovary Syndrome.

22. The method of claim 15, wherein the physiological condition is an ovulatory disorder.

23. The method of claim 15, wherein the physiological condition is a non-ovulatory disorder.

* * * * *